United States Patent [19]

Suchy

[11] 4,201,789
[45] May 6, 1980

[54] CYCLOPROPANECARBOXYLIC ACID NAPHTHYLMETHYL ESTER

[75] Inventor: Milos Suchy, Pfaffhausen, Switzerland

[73] Assignee: Hoffmann-La Roche Inc., Nutley, N.J.

[21] Appl. No.: 968,893

[22] Filed: Dec. 13, 1978

[30] Foreign Application Priority Data

Dec. 21, 1977 [LU] Luxembourg .......................... 78736

[51] Int. Cl.² ........................ C07C 69/74; A01N 9/24
[52] U.S. Cl. ..................................... 424/305; 560/124
[58] Field of Search ......................... 560/124; 424/305

[56] References Cited

U.S. PATENT DOCUMENTS

| 3,567,740 | 3/1971 | Matsui | 560/124 |
| 3,840,584 | 10/1974 | Crawford | 560/124 |

FOREIGN PATENT DOCUMENTS

| 44-25576 | 10/1969 | Japan | 560/124 |
| 44-27992 | 11/1969 | Japan | 424/305 |
| 44-27994 | 11/1969 | Japan | 424/305 |

Primary Examiner—Joseph E. Evans
Assistant Examiner—Michael Shippen
Attorney, Agent, or Firm—Jon S. Saxe; Bernard S. Leon; William M. Farley

[57] ABSTRACT

Cyclopropanecarboxylic acid naphthylmethyl ester, processes for its preparation, as well as pesticidal compositions which contain the naphthylmethyl ester as the active ingredient and methods of use of the pesticidal compositions are disclosed.

5 Claims, No Drawings

CYCLOPROPANECARBOXYLIC ACID NAPHTHYLMETHYL ESTER

SUMMARY OF THE INVENTION

This invention is directed to cyclopropanecarboxylic acid 2-naphthylmethyl ester of the formula

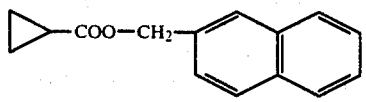
I as well as processes for its preparation. This invention is also directed to pesticidal compositions containing, as the active ingredient, the compound of formula I and methods for use of these pesticidal compositions.

DETAILED DESCRIPTION OF THE INVENTION

This invention is directed to cyclopropane-carboxylic acid 2-naphthylmethyl ester of the formula

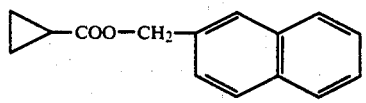
I

This invention is also directed to process for the preparation of this compound as well as pesticidal compositions, and methods for their use, which contain, as the active ingredient, the compound of formula I.

While the compound of formula I possesses systemic activity, it acts mainly as a direct ovicide. The compound is especially useful against insects and acarids.

The cyclopropanecarboxylic acid 2-naphthylmethyl ester of formula I is prepared by one of the procedures described below:

A. The esterification of an acid of the formula

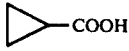
II, or a reactive derivative of the acid, with an alcohol of the formula

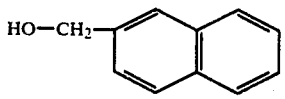
III

The expression "reactive derivative of an acid" refers to an acid halide, an acid anhydride, an imidazolide, an ester of a low-boiling alcohol, an alkali metal salt, a silver salt or a salt of a tertiary amine.

The esterification process using the acid of formula I is preferably carried out in a suitable inert solvent, at room temperature or at an elevated temperature. The reaction conditions are such as are suitable for eliminating water, e.g. in the presence of dicyclohexylcarbodiimide or by azeotropically distilling off the water formed in the catalyzed reaction mixture. If an acid halide is used as the reactive derivative of the acid of formula I, the reaction with the alcohol is carried out at room temperature in the presence of an acid acceptor, e.g. a tertiary amine such as pyridine or triethylamine and, preferably, in an inert solvent. The corresponding ester is obtained in high yield.

Preferred acid halides are the acid chlorides. Examples of suitable inert solvents include benzene, toluene and petroleum ether.

If an ester of a low-boiling alcohol is used as the reactive derivative of the acid of formula II the compound of formula I is prepared by heating the ester with the alcohol of the formula III in the presence of a base, preferably an alkali metal alcoholate which corresponds to the low-boiling alcohol of the ester employed, or in the presence of sodium hydride in an inert solvent such as toluene. The low-boiling alcohol, liberated during the reaction, is removed by fractional distillation.

Examples of low-boiling alcohols include methanol and ethanol.

If an imidazolide is used as the reactive derivative of the acid of formula II, the compound of formula I is prepared by reacting the imidazolide with the alcohol of formula III, in the presence of a catalytic amount of an alkali metal alcoholate, or with an alkali metal alcoholate of the alcohol of formula III. The reaction is preferably carried out at room temperature in an inert solvent, such as tetrahydrofuran or dimethoxyethane.

If an acid anhydride is used as the reactive derivative of the acid of the formula II, the compound formula I is prepared by reacting the acid anhydride with the alcohol of the formula III at room temperature or, preferably, with heating and in the presence of a solvent such as toluene or xylene.

B. The esterification of an acid of the formula

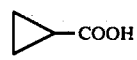
II, or a reactive derivative of the acid, with a compound of the formula

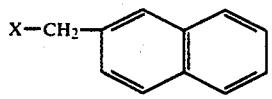
IV wherein X is chlorine, bromine, iodine, mesyloxy or tosyloxy.

These compounds of formula IV are, thus, reactive derivatives of the alcohol of formula III. The reactive derivatives are the halides or sulfonic acid esters.

If a halide or sulfonic acid ester is used as the reactive derivative of the alcohol of formula III (i.e. the compound of formula IV), the compound of I is prepared by reacting the halide or sulfonic acid ester with the acid of formula II. The reaction is carried out in an organic solvent such as acetone, methyl ethyl ketone, diethyl ketone, dimethylformamide, dimethyl sulphoxide, benzene or toluene and in the presence of a base, preferably potassium carbonate, the reaction temperature can range, preferably, from about 30° C. to the boiling point of the solvent. After completion of the reaction, the mixture is poured into an inorganic acid, preferably dilute hydrochloric acid, dilute sulphuric acid, dilute phosphoric acid or dilute nitric acid. The acid solution is extracted with hexane the hexane is distilled off and the residue is purified by chromatography on silica gel or aluminum oxide and/or by distillation.

This invention is also directed to pesticidal compositions which comprise inert carrier material and, as the active ingredient, the compound of formula I, i.e. cyclopropanecarboxylic acid 2-naphthylmethyl ester. These pesticidal compositions contain, as the inert carrier material, at least one of the following ingredients: carrier material, wetting agents, inert diluents and solvents.

The compound of formula I, cyclopropanecarboxylic acid 2-naphthylmethyl ester, is water soluble. Thus, the usual methods of formulation of insoluble materials can be followed. For example, cyclopropanecarboxylic acid 2-naphthylmethyl ester can be dissolved in a water-immiscible solvent such as a high-boiling hydrocarbon which, preferably, contains dissolved emulsifiers. The solution acts as a selfemulsifiable oil when added to water.

The compound of the formula I can also be mixed with a wetting agent, with or without an inert diluent, to form a wettable powder which is soluble or dispersible in water. Cyclopropanecarboxylic acid 2-naphthylmethyl ester can be mixed with an inert diluent to form a solid or pulverulent powder.

Suitable inert diluents, with which the compound of the formula I can be processed, are solid inert media including pulverulent or finely divided solids such as clays, sand, talc, mica, fertilizers and the like. The resulting compositions can be either dusts or materials of relatively large particle size.

Wetting agents, suitable for use with cyclopropanecarboxylic acid 2-naphthylmethyl ester, can be anionic, cationic or non-ionic.

Examples of anionic wetting agents include soaps, fatty sulfate esters such as sodium dodecyl-sulfate, sodium octadecyl-sulfate and sodium cetyl-sulfate, fatty-aromatic sulfonates, such as alkylbenzene-sulfonates, or butylnaphthalenesulfonates, and the more complex fatty sulfonates, such as the amide condensation products of oleic acid and N-methyltaurine or the sodium salt of dioctylsuccinate.

Examples of cationic wetting agents include cetyltrimethylammonium bromide and the like.

Examples of non-ionic wetting agents include, for example, condensation products of fatty acids, fatty alcohols or fatty-alkyl-substituted phenols with ethylene oxide, fatty acid esters and ethers of sugars or of polyhydric alcohols, condensation products of these fatty acid esters and ethers of sugars or of polyhydric alcohols with ethylene oxide or block copolymers of ethylene oxide and propylene oxide.

The pesticidal compositions of this invention can also be used in aerosol form using, in addition to the propellant gas, carrier material comprising a co-solvent and a wetting agent. Suitable propellant gases included the polyhalogenated alkanes such as dichlorodifluoromethane.

The pesticidal compositions of this invention can also contain other active ingredients such as synergistic agents and other active insecticides, bactericides and fungicides.

Cyclopropanecarboxylic acid 2-naphthylmethyl ester is particularly valuable as an insecticide and acaricide, especially against sucking pests such as white flies, aphids and spiders such as tetranychidae, esiophyidae and ixodoidea. The compound acts as a direct insecticide and mainly as a direct ovicide. It thus reduces, on a long term basis, any increase in the insect population. Cyclopropane-carboxylic acid 2-naphthylmethyl ester also possesses systemic action. Its action as an acaricide is a preferred aspect of this invention.

The present invention is also concerned with a method for the treatment of animals and locus, e.g. plants and soil, subject to or subjected to attack by pests free from such attack, which method comprises applying to said animals or locus an effective amount of the pesticidal composition as defined hereinabove.

In general, cyclopropanecarboxylic acid 2-naphthylmethyl ester can be used in different concentrations depending on its intended end use. For example, the compound is applied at a concentration of from about 100 to about 2,000 g/ha for combatting pests on plants. To combat ectoparasites on animals, the animals are conveniently dipped in a solution containing from about 100 to about 1,000 ppm of cyclopropanecarboxylic acid 2-naphthylmethyl ester. Alternatively, the animals can be sprayed with a solution of the same concentration.

The acute toxicity of cyclopropane carboxylic acid 2-naphthylmethyl ester is greater than 1,000 mg/kg. Thus, it is of extremely low toxicity to vertebrae.

The following Examples illustrate the invention.

EXAMPLE 1

2 g of 2-hydroxymethylnaphthalene are dissolved in 20 ml of benzene and 0.7 ml of pyridine. 1.2 ml of cyclopropanecarboxylic acid chloride in 10 ml of benzene are added and the mixture is heated to 70° C. for 15 minutes. The resulting product is poured into water and extracted with ether. The ether extract is washed with water, dried over sodium sulfate and evaporated under reduced pressure. The product, cyclopropanecarboxylic acid 2-naphthylmethyl ester is purified by adsorption on silica gel, $n_D^{20}$: 1.5900.

EXAMPLE 2

1.7 g of cyclopropanecarboxylic acid are dissolved in 20 ml of acetone. 0.9 g of potassium hydroxide is added to the solution and the mixture is heated to 55° C. After 6.2 g of 2-bromo-methylnaphthalene are added, the mixture is then heated for 12 hours to 65° C. The resulting product is poured into 150 ml of 2 N HCl and extracted with hexane. The hexane extract is washed with water, dried over sodium sulfate and evaporated under reduced pressure. The product, cyclopropanecarboxylic acid 2-naphtylmethyl ester, is purified by adsorption on silica gel, $n_D^{20}$: 1.5900.

EXAMPLE 3

This Example illustrates the activity of cyclopropanecarboxylic acid 2-naphthylmethyl ester on fruit tree spider mites. A known pesticide, cyclopropanecarboxylic acid hexadecyl ester, was used as the standard.

Apple trees (Star Crimson) were treated with a wettable powder containing cyclopropanecarboxylic acid 2-naphthylmethyl ester as the active ingredient. The concentration of active ingredient was 0.075% and the amount of liquor used in 2,4000 liters of the solution per hectare were used. The plot size contained one apple tree and experiments were carried out with four plots for each compound.

Thirty-eight days after treatments, the trees were examined for the number of fruit tree spider mites per leaf (10 leaves/tree). Results are tabulated below for each tree.

| Compound | Average No. of spider mites/leaf | | | |
|---|---|---|---|---|
| | 1st | 2nd | 3rd | 4th |
| Untreated | 74.5 | 17.6 | 25.2 | 19.6 |
| Cyclopropanecarboxylic acid 2-naphthylmethyl ester | 4.1 | 2.4 | 0.9 | 7.7 |
| Cyclopropanecarboxylic acid hexadecyl ester | 39.9 | 10.2 | 30.8 | 44.8 |

The economically acceptable damage threshold is 8–10 fruit tree spider mites/tree.

Using WILCOXON'S test, there is a significant different between the average number of spider mites on the plots treated with cyclopropanecarboxylic acid 2-naphthylmethyl ester and the plots treated with the standard. There is no significant difference between the plots treated with the standard and the untreated plots (5% level).

EXAMPLE 4

This example illustrates both the activity of cyclopropanecarboxylic acid 2-naphthylmethyl ester against *Tetranychus urticae* and the ultra-violet stability of the compound.

The following compounds were evaluated:

| Compound | | |
|---|---|---|
| A | (naphthyl-CH₂-O-C(=O)-cyclopropyl) | (Cyclopropanecarboxylic acid) (2-naphthylmethyl ester) |
| B | (naphthyl-CH₂-C(=O)-O-CH₂-cyclopropyl) | |
| C | (naphthyl-C(=O)-O-CH₂-cyclopropyl) | |

Young potted kidney bean plants, in the two-leaf stage, are sprayed with an acetone solution of an active ingredient. The dosage rate was $10^{-5}$ grams of active ingredient per square centimeter.

After the spray treatment, the plants are incubated for seven days under ultraviolet light (Phillips TLA 40 W/05). Following the incubation period, 3 cm diameter discs are cut from the plants and infected with 8–10 adult *Tetranychus urticae*.

The adult animals are removed one day later and the leaf discs containing eggs are kept at 25° C. and 60% atmospheric humidity for 6 days. Untreated and acetone-treated plants served as controls.

The reslts, tabulated below, are expressed in percent reduction of the hatching rate and of the survival rate of the first larvae as compared to the controls.

| Compound | % Reduction |
|---|---|
| A | 95 |
| B | 5 |
| C | 5 |

The above results are averages of 10 experiments (Wilcoxon test, p=0.01). These results also indicate the pronounced µv-stability of cyclopropanecarboxylic acid 2-naphthylmethyl ester.

EXAMPLE 5

This example illustrates the activity of cyclopropanecarboxylic acid 2-naphthylmethyl ester against a sensitive strain of *Tetranychus urticae*.

Kidney bean plants with a well-developed leaf are infected with ten female animals of a sensitive strain of *Tetranychus urtricae*. After egg laying (2 days after infection) the female animals are removed and the plants are sprayed with 20 ml of an aqueous emulsion of the active ingredient.

Seven days after treatment, the numbers of hatched and non-hatched eggs are counted. Results for the various dosage rates are tabulated below.

| Compound | Dosage/ | Reduction | | |
|---|---|---|---|---|
| | | 0.1% | 0.03% | 0.01% |
| A | | 100 | 98 | 87 |
| | | 100 | 97 | 86 |
| | | 100 | 94 | 68 |
| | | 99 | 91 | 34 |
| | | 99 | 91 | 30 |
| | | 99 | 80 | 14 |
| B | | 100 | 98 | 17 |
| | | 100 | 98 | 16 |
| | | 99 | 95 | 12 |
| | | 98 | 83 | 6 |
| | | 97 | 71 | 5 |
| | | 86 | 64 | — |
| C | | 100 | 73 | 22 |
| | | 98 | 71 | 12 |
| | | 97 | 63 | 6 |
| | | 96 | 59 | 3 |
| | | 91 | 43 | 2 |
| | | 85 | 2 | — |

The dosage is expressed as percent of active ingredient. 0.1% of active ingredient is equal to an applied dosage of about $10^{-6}$ g of active ingredient per square centimeter.

On the Wilcoxon-Mann-Whitney U Test, p=0.05 (one-sided).

EXAMPLE 6

This Example illustrates the preparation of an emulsifiable concentrate.

The following ingredients are admixed.

| Ingredient | Amount |
|---|---|
| Cyclopropanecarboxylic acid 2-naphthylmethyl ester | 500 g |
| Condensation product of alkylphenols with about 25 mols of ethylene oxide and calcium dodecylbenzenesulfonate in a ratio of 3:1 | 100 g |
| Expoxidized soy bean oil with an oxican oxygen content of about 6% | 25 g |
| Butylated hydroxytoluene | 10 g |
| Xylene | to 1 liter |

I claim:

1. Cyclopropanecarboxylic acid 2-naphthylmethyl ester.

2. An insecticidal and acaricidal composition which comprises inert carrier material and, as the active ingredient, an amount of cyclopropanecarboxylic acid 2-naphthylmethyl ester which is effective as an insecticide and acaricide.

3. A method of killing insects and acarids which comprises application of an insecticidal and acaricidal effective amount of the composition of claim 2.

4. The method of claim 3 wherein the insects or acarids are spider mites.

5. A method for providing a plant of locus subject to or subjected to attack by insects or acarids free from such attack which comprises applying to said plant or locus an insecticidal or acaricidal effective amount of the composition of claim 2.

* * * * *